US006307014B1

(12) United States Patent
Furie et al.

(10) Patent No.: US 6,307,014 B1
(45) Date of Patent: Oct. 23, 2001

(54) CONOPEPTIDES

(76) Inventors: Bruce Furie; Barbara C. Furie, both of 175 Oakland St., Wellesly, MA (US) 02481; Johan Stenflo, Artholmsvagen 196, S-21620 Malmo (SE); Alan C. Rigby, 41 Avenue Louis Pasteur, Boston, MA (US) 02215; Peter Roepstorff, Kolding Landevej 43, DK-7000 Fredericia (DK)

( * ) Notice: Subject to any disclaimer, the term of this patent is extended or adjusted under 35 U.S.C. 154(b) by 0 days.

(21) Appl. No.: 09/136,769

(22) Filed: Aug. 19, 1998

(51) Int. Cl.[7] .......................... C07K 14/00; C07K 14/435
(52) U.S. Cl. .......................... 530/324; 530/326; 530/333; 530/344; 514/8; 514/12; 514/13
(58) Field of Search .................... 514/8, 12, 13; 530/324, 326, 333, 344

(56) References Cited

PUBLICATIONS

Chandler et al., "Polyamine–like actions of peptides derived from conatokin–G, an N–methyl–D–aspartate (NMDA) antagonist." *J. Biol. Chem.*, 268:17173–17178 (1993).

Cruz et al., "A preliminary study of Conus venom protein." *Veliger*, 18:302–308 (1976).

Cruz et al., "Conus peptides: Phylogenetic range of biological activity." *Biol. Bull.*, 183:159–164 (1992).

Czerwiec et al., "Vitamin K–dependent carboxylase: Comparison of the bovine y–carboxylase with the y–carboxylase from the marine snail." *Blood 88*, (Suppl. 1):523a (1996).

Fainzilber et al., "Mollusc–specific toxins from the venom of Conus textile neovicarius." *Eur. J. Biochem.*, 588–595 (1991).

Haack et al., "Conantokin–T: a y–carboxyglutamate containing peptide with N–methyl–D–aspartate antagonist activity" *J. Biol. Chem.*, 265:6025–6029 (1989).

McIntosh et al., "y–carboxyglutamate in a neuroactive toxin," *J. Biol. Chem.*, 259:14343–14346 (1984).

Mena et al., "Conantokin–G: A novel peptide antagonist to the N–methyl–D–aspartic (NMDA) receptor." *Neurosci. Lett.*, 118:241–244 (1990).

Nakamura et al., "Mass spectrometric–based revision of the structure of a cysteine–rich peptide toxin with y–carboxyglutamic acid, TxVIIA, from the sea snail, Conus textile," *Protein Sci.*, 5:524–530 (1996).

Olivera et al., "Peptide neurotoxins from fish–hunting cone snails." *Science*, 230:1338–1343 (1985).

Olivera et al., "Diversity of Conus neuropeptides." *Science*, 249:257–263 (1990).

Olivera et al., "Conotoxins." *J. Biol. Chem.*, 33:22067–22070 (1991).

Rigby et al., "Three dimensional structure of a y–carboxyglutamic acid–containing conotoxin, conantokin–G, from the marine cone snail Conus geographus: The metal–free conformer." *Biochemistry* 36:6906–6914 (1997).

Rigby et al., "The role of y–carboxyglutamic acid in the calcium–induced structural transition of conantokin–G, a contoxin from the marine cone snail Conus geographus." *Biochemistry* 36:15677–15684 (1997).

Skjaerbaek et al., "Determination of the solution structures of conantokin–G and conantokin–T by CD and NMR spectroscopy." *J. Biol. Chem.*, 272:2291–2299 (1997).

Woodward et al., "Constant and hypervariable regions in conotoxin propeptides." *EMBO J.*, 9:1051–1020 (1990).

Zhou et al., "Synthetic analogues of conantokin G: NMDA antagonists acting through a novel polyamine–coupled site." *J. Neurochem.*, 66:620–628 (1996).

*Primary Examiner*—Christopher S. F. Low
*Assistant Examiner*—Anish Gupta

(57) ABSTRACT

Substantially pure conopeptides containing γ-carboxyglutamic acid are disclosed.

14 Claims, 6 Drawing Sheets

Gly Glu Gla Gla Leu Gln Gla Asn Gln Gla Leu Ile Arg Gla Lys Ser Asn NH₂ (SEQ ID NO: 23)

Conantokin G

Fig. 1a

Gly Glu Gla Gla Tyr Gln Lys Met Leu Gla Asn Leu Arg Gla Ala Glu Val Lys Lys Asn Ala NH₂ (SEQ ID NO: 24)

Conantokin T

Fig. 1b

Cys Gly Gly Tyr Ser Thr Tyr Cys Gla Val Asp Ser Gla Cys Cys Ser Asp Asn Cys Val Arg Ser Tyr Cys Thr Leu Phe (SEQ ID NO: 25)

Ctx TxVIIA

Fig. 1c

P6.1 (1)   Asp Val Pro Gla Ile Val Leu Gla Phe Met Cys Pro Val Ile Cys
Gly Asn Gly Phe Gly Gla Glu Tyr Cys Asn Cys Thr (SEQ ID NO: 12)

Fig. 2a

P7.1 (2)   Ser Cys Asp Ser Gla Phe Ser Ser Gla Phe Cys Gla Arg Pro Gla Gla Ser Cys
Ser Cys Ser Thr His Thr Cys Cys His Trp Ala Arg Arg Asp Gln Cys Met
Lys Pro Gln Arg Cys Ile Ser Ala Gln Lys Gly Asn (SEQ ID NO: 13)

Fig. 2b

P8.1A   (3)   Arg OHP Gla Cys Cys Ser Asp Pro Arg Cys Asn Ser Ser His Pro
Gla Leu Cys Gly $NH_2$ (SEQ ID NO: 14)

Fig. 2c

P8.2B (4)   Gly Cys Asn Asn Ser Cys Gln Gla His Ser Asp Cys Gla Ser His Cys Ile
Cys Thr Phe Arg Gly Cys Gly Ala Val Asn $NH_2$ (SEQ ID NO: 15)

Fig. 2d

P9.1B (5)   Cys Ile Pro Gla Gly Ser Ser Cys Ser Ser Ser Gly Ser Cys Cys His Lys Ser
Cys Cys Arg Trp Thr Cys Asn Gln Pro Cys Leu (SEQ ID NO: 16)

Fig. 2e

P10.3 (6)   Gly Met BrW Gly Gla Cys Lys Asp Gly Leu Thr Thr Cys Leu Ala OHP
Ser Gla Cys Cys Ser Gla Asp Cys Gla Gly Ser Cys Thr Met
BrW (SEQ ID NO: 17)

Fig. 2f

P11.1 (7) Gla Cys Cys Gla Asp Gly BrW Cys Cys Thr Ala Ala OHP (SEQ ID NO: 18)

Fig. 3a

P12.3 (8) Ser Cys Ser Asp Asp Trp Gln Tyr Cys Gla Ser OHP Thr Asp Cys Cys Ser BrW Asp Cys Asp Val Val Cys Ser (SEQ ID NO: 19)

Fig. 3b

P13.1 (9) Ala BrW Cys His OHP Cys OHP Phe Gla Tyr (SEQ ID NO: 20)

Fig. 3c

P13.2 (10) Asn Cys Ser Asp Asp Trp Gln Tyr Cys Gla Ser OHP Ser Asp Cys Cys Ser BrW Asp Cys Asp Val Val Cys Ser (SEQ ID NO: 21)

Fig. 3d

P14.1 (11) Leu Cys OHP Asp Tyr Thr Gla OHP Cys Ser His Ala His Gla Cys Cys Ser BrW Asn Cys Tyr Asn Gly His Cys Thr Gly (SEQ ID NO: 22)

Fig. 3e

CONOPEPTIDES

STATEMENT AS TO FEDERALLY SPONSORED RESEARCH

The invention described herein was supported in whole or in part by grants HL 42443 and HL 18834 from the National Institutes of Health. The government may have certain rights in the invention.

BACKGROUND OF THE INVENTION

The invention relates to conopeptides.

Cone snails (Conus) are widely dispersed marine gastropods that prey on fish, marine worms, and mollusks. Cone snails are venomous predators that elaborate peptide toxins in their venom ducts; the venom flows from the venom ducts through hollow stinging radular teeth, into the prey of the snails.

Several of these peptide toxins, generically referred to as conopeptides, have been characterized. The conotoxins are small peptides with a high density of disulfide bonds; cysteine residues can represent up to 50% of the amino acids in some conotoxins. Conotoxins target nicotinic acetylcholine receptors, sodium channels, and calcium channels, and thus behave as potent receptor antagonists.

Another group of peptide toxins includes the conantokins. These peptides, in contrast to other conotoxins, generally contain no cysteine residues. Conantokins are characterized by the presence of one or more γ-carboxyglutamic acid (Gla) residue. Conantokin-G, isolated from the cone snail *Conus geographus*, has 17 residues, 5 of which are Gla residues; conantokin-T, isolated from *Conus tulipa*, has 21 residues, 4 of which are Gla residues. Many of the conantokins have N-methyl-D-aspartate (NMDA) antagonist activity.

Still other conopeptides have some of the characteristics of both the conotoxins and the conantokins. For example, the conopeptide Ctx TxVIIA, isolated from *Conus textile*, contains both Gla residues and cysteine residues.

SUMMARY OF THE INVENTION

The invention features substantially pure Gla-containing peptides. The peptides have the amino acid sequences:

(a) Asp Val Pro $X_1$ Ile Val Leu $X_2$ Phe Met Cys Pro Val Ile Cys Gly Asn Gly Phe Gly $X_3$ Glu Tyr Cys Asn Cys Thr (SEQ ID NO:1), where each of $X_1$, $X_2$, and $X_3$ is independently selected from Glu and Gla, provided that at least one of $X_1$, $X_2$, and $X_3$ is Gla;

(b) Ser Cys Asp Ser $X_4$ Phe Ser Ser $X_5$ Phe Cys $X_6$ Arg Pro $X_7$ $X_8$ Ser Cys Ser Cys Ser Thr His Thr Cys Cys His Trp Ala Arg Arg Asp Gln Cys Met Lys Pro Gln Arg Cys Ile Ser Ala Gln Lys Gly Asn (SEQ ID NO:2), where each of $X_4$, $X_5$, $X_6$, $X_7$, and $X_8$ is independently selected from Glu and Gla, provided that at least one of $X_4$, $X_5$, $X_6$, $X_7$, and $X_8$ is Gla;

(c) Arg $X_9$ $X_{10}$ Cys Cys Ser Asp Pro Arg Cys Asn Ser Ser His Pro $X_{11}$ Leu Cys Gly (SEQ ID NO:3), where $X_9$ is Pro or OHP and each of $X_{10}$ and $X_{11}$ is independently selected from Glu and Gla, provided that at least one of $X_{10}$ and $X_{11}$ is Gla;

(d) Gly Cys Asn Asn Ser Cys Gln $X_{12}$ His Ser Asp Cys $X_{13}$ Ser His Cys Ile Cys Thr Phe Arg Gly Cys Gly Ala Val Asn (SEQ ID NO:4), where each of $X_{12}$ and $X_3$ is independently selected from Glu and Gla, provided that at least one of $X_{12}$ and $X_{13}$ is Gla;

(e) Cys Ile Pro Gla Gly Ser Ser Cys Ser Ser Ser Gly Ser Cys Cys His Lys Ser Cys Cys Arg Trp Thr Cys Asn Gln Pro Cys Leu (SEQ ID NO:5);

(f) Gly Met $X_{14}$ Gly $X_{15}$ Cys Lys Asp Gly Leu Thr Thr Cys Leu Ala $X_{16}$ Ser $X_{17}$ Cys Cys Ser $X_{18}$ Asp Cys $X_{19}$ Gly Ser Cys Thr Met $X_{20}$ (SEQ ID NO:6), where each of $X_{14}$ and $X_{20}$ is independently selected from Trp and BrW, each of $X_{15}$, $X_{17}$, $X_{18}$, and $X_{19}$ is independently selected from Glu and Gla, provided that at least one of $X_{15}$, $X_{17}$, $X_{18}$, and $X_{19}$ is Gla, and $X_{16}$ is Pro or OHP;

(g) $X_{21}$ Cys Cys $X_{22}$ Asp Gly $X_{23}$ Cys Cys Thr Ala Ala $X_{24}$ (SEQ ID NO:7), where each of $X_{21}$ and $X_{22}$ is independently selected from Glu and Gla, provided that at least one of $X_{21}$ and $X_{22}$ is Gla, $X_{23}$ is Trp or BrW, and $X_{24}$ is Pro or OHP;

(h) Ser Cys Ser Asp Asp Trp Gln Tyr Cys Gla Ser $X_{25}$ Thr Asp Cys Cys Ser $X_{26}$ Asp Cys Asp Val Val Cys Ser (SEQ ID NO:8), where $X_{25}$ is Pro or OHP and $X_{26}$ is Trp or BrW;

(i) Ala $X_{27}$ Cys His $X_{28}$ Cys $X_{29}$ Phe Gla Tyr (SEQ ID NO:9), where $X_{27}$ is Trp or BrW and each of $X_{28}$ and $X_{29}$ is independently selected from Pro and OHP;

(j) Asn Cys Ser Asp Asp Trp Gln Tyr Cys Gla Ser $X_{30}$ Ser Asp Cys Cys Ser $X_{31}$ Asp Cys Asp Val Val Cys Ser (SEQ ID NO:10), where $X_{30}$ is Pro or OHP and $X_{31}$ is Trp or BrW; or (k) Leu Cys $X_{32}$ Asp Tyr Thr $X_{33}$ $X_{34}$ Cys Ser His Ala His $X_{35}$ Cys Cys Ser $X_{36}$ Asn Cys Tyr Asn Gly His Cys Thr Gly (SEQ ID NO:11), where each of $X_{32}$ and $X_{34}$ is independently selected from Pro and OHP, and each of $X_{33}$ and $X_{35}$ is independently selected from Glu and Gla, provided that at least one of $X_{33}$ and $X_{35}$ is Gla, and $X_{36}$ is Trp or BrW.

"Gla" represents a γ-carboxyglutamic acid residue; "OHP" represents a hydroxyproline residue; and BrW represents a bromotryptophan residue.

One or more of the residues of these peptides may be glycosylated. The termini of the peptides may be modified as well; for example, the C terminus may be amidated.

By "substantially pure" is meant that a conopeptide of the invention has been separated from components which naturally accompany it, or which are generated during its preparation or extraction. Preferably the peptide is at least 90%, more preferably at least 95%, and most preferably at least 99%, by weight, free from the other peptides and molecules with which it is naturally associated. The purity of the peptides can be measured by any appropriate method, for example, column chromatography, polyacrylamide gel electrophoresis, or HPLC analysis.

The peptides of the invention have a variety of applications. They can be used as medicinal agents, for example, as pain medications. They can also be used in veterinary applications; the peptides may be used to temporarily stun, yet not kill, fish and other marine life. Such an application is useful when studying marine life forms.

BRIEF DESCRIPTION OF THE DRAWINGS

FIGS. 1a, 1b, and 1c are amino acid sequences of three previously-known Gla-containing conotoxins.

FIGS. 2a–2f are amino acid sequences of novel conopeptides of the invention.

FIGS. 3a–3e are amino acid sequences of novel conopeptides of the invention.

DETAILED DESCRIPTION

Figure 4:
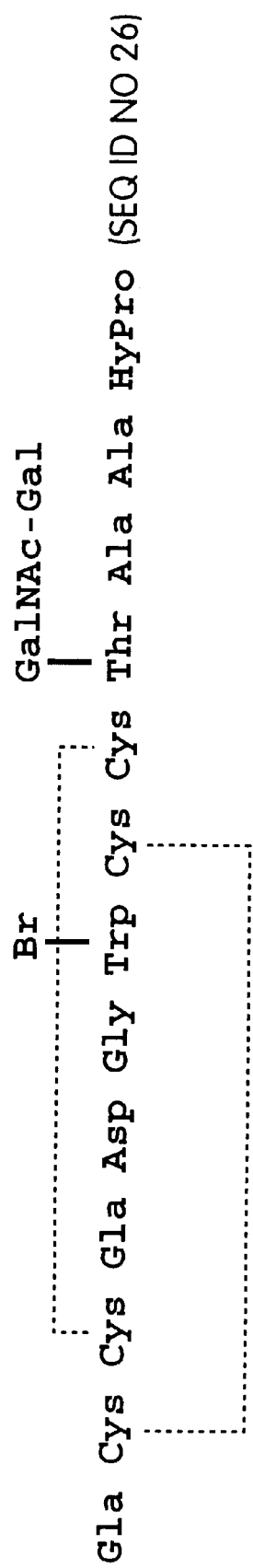
FIG. 4 is an amino acid sequence of the novel peptide P11.1.

The conopeptides of the invention contain one or more γ-carboxyglutamic acid residues. The γ-carboxyglutamic acid content of these peptides can be as much as 25% of the peptides.

γ-Carboxyglutamic acid (Gla) is a metal-binding amino acid that is synthesized via a post-translational mechanism that involves the γ-carboxylation of specific glutamic acid residues. The modification of substrate peptide residues is catalyzed by the vitamin K-dependent enzyme γ-glutamyl carboxylase in a reaction that requires molecular oxygen, carbon dioxide, and reduced vitamin K.

The venom of all Conus species tested—*Conus textile, Conus striatus, Conus imperialis, Conus ebraeus, Conus miles, Conus distans, Conus vitulinus, Conus pennaceus, Conus leopardus, Conus marmoreous, Conus tulipa* and *Conus geographus*—contains γ-carboxyglutamic acid.

Conantokin G, conantokin T, and conotoxin Ctx TxVIIA (FIG. 1) are active as neurotoxins. Chemically synthesized peptides based upon conantokin sequences are also pharmacologically active neurotoxins. Substitution of γ-carboxyglutamic acid residues by glutamic acid residues in some chemically synthesized conotoxin analogs yields pharmacologically inert peptides. The presence of at least one y-carboxyglutamic acid residue therefore appears to be critical to the biologic activity of these peptides.

Many of the conantokins are NMDA receptor antagonists. As the NMDA receptor is involved in a broad spectrum of CNS disorders, conantokins are expected to be useful in treating these disorders. In addition, it is believed that NMDA antagonists can reduce the tolerance to analgesics that can occur after repeated administration of analgesics.

We have now discovered that the novel peptide P11.1 (FIG. 3a) causes tremors and seizures in young mice. Based on the biological activity of this peptide and on the biological activity of other conopeptides, the peptides of the invention may be useful for treating CNS disorders and in the management of chronic pain.

The peptides can also be used, by humans, for the purpose for which cone snails use them; i.e., the peptides can be used to paralyze fish and other marine animals temporarily. This can be useful in the collection of rare fish species for aquariums and research facilities.

For this use, the peptide is loaded into an underwater-use spring or $CO_2$-powered spear gun, which is used according to conventional methods.

Synthesis of Conopeptides

The conopeptides can be synthesized using solid-phase techniques, as described below, using an automatic synthesizer. Typically, synthesis begins at the C-terminus of the peptide by coupling a protected α-amino acid to a suitable resin, for example, a paramethylbenzhydrylamine (MBHA) rink resin.

Following solid-phase synthesis, the peptides can be modified. For example, oxidation and cyclization to form disulfide bonds between Cys residues can be effected. To effect the cyclization, the fully protected peptide can be cleaved from the resin support to yield the protected intermediate; the intermediate can then be air-oxidized, cyclized, and deprotected.

The peptides can also be isolated from *C. textile* venom. Live snails can be obtained from Fiji; alternatively, frozen snails can be obtained from Vietnam. The venom is extracted from the venom ducts of the snails and subjected to purification by gel-filtration and reverse-phase HPLC. The purified peptides are then sequenced via automated Edman degradation to determine the primary structure of the peptides. The peptides obtained in this manner may be post-translationally modified; for example, they may be brominated, glycosylated, or hydroxylated.

There now follow particular examples of the preparation of peptides according to the invention. These examples are provided for the purpose of illustrating the invention, and should not be construed as limiting.

EXAMPLE 1
Synthesis and Characterization of Conopeptides

The peptides of the invention are synthesized as follows. Each peptide is synthesized using solid phase Fmoc[N-(9-fluorenyl)methoxycarbonyl/N-methylpyrrolidine] chemistry on an Applied Biosystems model 430A peptide synthesizer, using the techniques described in Jacobs et al., *J. Biol. Chem.* 269:25494–25501 (1994). To obtain C-terminal amidation, rink amide MBHA resin is used (NovaBiochem), and the C-terminal amino acid is double-coupled to the MBHA resin under standard conditions. The peptide is cleaved from the resin in triethylsilane/1,2-ethanedithiol/TFA (5:5:90) for 2.5 hours at 25° C. with constant stirring.

The peptide sample is lyophilized and then purified by reverse phase HPLC using a preparative reverse phase $C_{18}$ Bio-Rad Hi-Pore 318 column ($RPC_{18}$, 21.5 mm×250 mm) and a Beckman system Gold HPLC system. The column is developed with a linear gradient from 10 to 40% acetonitrile in the presence of 0.1% trifluoroacetic acid at a flow rate of 8.0 mL/minute and monitored at 214 nm. The peak containing the majority of the peptide is pooled and rechromatographed on a reverse phase HPLC system using a Vydac 218TP 5 μm column (4.6 mm×250 mm) using the same linear gradient at a flow rate of 1.0 mL/minute.

The purified peptide is subjected to MALDI-TOF mass spectroscopy on a Voyager Linear MALDI-TOF spectrometer (PerSeptive Biosystems). The mass spectroscopy analysis is performed with a nitrogen laser at 337 nm, employing either linear mode positive or negative ionizations. The accelerating voltage is 30 kV, and spectra are generated from the sum of 37 averaged scans. The peptide is sequenced by automated Edman degradation using a Perkin Elmer ABI Procise protein sequencer.

EXAMPLE 2
Isolation of Peptides from *C. textile* Venom

Live *C. textile* snails were imported from Fiji; the snails were individually packaged in sea water in doubled polyethylene bags and shipped by air.

55 mg of Gla-containing conopeptides were extracted from five venom ducts of *C. textile*. The peptides were subjected to gel-filtration on Sephadex G50. The column fractions were monitored by direct Gla analysis and $OD_{280}$. The chromatogram included six major peaks detected by quantitative Gla analysis. These peaks were further purified by reverse phase HPLC, and the purified peptides were sequenced via automated Edman degradation to determine the primary structures of the peptides. γ-Carboxyglutamic acid was rigorously identified by ion exchange and HPLC by comparison to an authentic chemical standard. The presence of γ-carboxyglutamic acid was further confirmed by the quantitative formation of glutamic acid upon thermal decarboxylation of the γ-carboxyglutamic acid.

Eleven novel Gla-containing peptides were identified and partially characterized. The sequences of these peptides are shown below and in FIGS. 2 and 3.

Asp Val Pro Gla Ile Val Leu Gla Phe Met Cys Pro Val Ile Cys Gly Asn Gly Phe Gly Gla Glu Tyr Cys Asn Cys Thr (1) (SEQ ID NO:12);

Ser Cys Asp Ser Gla Phe Ser Ser Gla Phe Cys Gla Arg Pro Gla Gla Ser Cys Ser Cys Ser Thr His Thr Cys Cys His Trp Ala Arg Arg Asp Gln Cys Met Lys Pro Gln Arg Cys Ile Ser Ala Gln Lys Gly Asn (2) (SEQ ID NO:13);

Arg OHP Gla Cys Cys Ser Asp Pro Arg Cys Asn Ser Ser His Pro Gla Leu Cys Gly (3) (SEQ ID NO:14);

Gly Cys Asn Asn Ser Cys Gln Gla His Ser Asp Cys Gla Ser His Cys Ile Cys Thr Phe Arg Gly Cys Gly Ala Val Asn (4) (SEQ ID NO:15);

Cys Ile Pro Gla Gly Ser Ser Cys Ser Ser Ser Gly Ser Cys Cys His Lys Ser Cys Cys Arg Trp Thr Cys Asn Gln Pro Cys Leu (5) (SEQ ID NO:16);

Gly Met BrW Gly Gla Cys Lys Asp Gly Leu Thr Thr Cys Leu Ala OHP Ser Gla Cys Cys Ser Gla Asp Cys Gla Gly Ser Cys Thr Met BrW (6) (SEQ ID NO:17);

Gla Cys Cys Gla Asp Gly BrW Cys Cys Thr Ala Ala OHP (7) (SEQ ID NO:18);

Ser Cys Ser Asp Asp Trp Gln Tyr Cys Gla Ser OHP Thr Asp Cys Cys Ser BrW Asp Cys Asp Val Val Cys Ser (8) (SEQ ID NO:19);

Ala BrW Cys His OHP Cys OHP Phe Gla Tyr (9) (SEQ ID NO:20);

Asn Cys Ser Asp Asp Trp Gln Tyr Cys Gla Ser OHP Ser Asp Cys Cys Ser BrW Asp Cys Asp Val Val Cys Ser (10) (SEQ ID NO:21); and Leu Cys OHP Asp Tyr Thr Gla OHP Cys Ser His Ala His Gla Cys Cys Ser BrW Asn Cys Tyr Asn Gly His Cys Thr Gly (11) (SEQ ID NO:22).

EXAMPLE 3

Isolation of P11.1 (Sigma-VIII Tx)

Frozen cone snails (*Conus textile*) were obtained from Vietnam. Lyophilized venom extract (200 mg, from five snails) was dissolved in 0.2 M ammonium acetate and chromatographed on a Sephadex G 50 superfine column (2.5×92 cm) equilibrated with 0.2 M ammonium acetate buffer, pH 7.5, and eluted with a flow rate of 9.2 ml/hour. The material in the major Gla-containing peak was purified on a reverse phase column (HyCrom C18, 5$\mu$, 10×250 mm) in 0.1% TFA, and eluted with an acetonitrile gradient. A total of 1.1 mg of peptide (560 nanomoles) was obtained. The amino acid composition was determined following acid hydrolysis, except for Gla, which was determined after alkaline hydrolysis. Monosaccharides were analyzed as described in Karlsson et al., *Anal. Biochem.* 224:538–541 (1995). N-terminal sequence determinations (Perkin Elmer ABI Procise 494 sequencer) were performed before and after reduction and alkylation (vinyl pyridine) of disulfide bonds. To identify Gla in the sequence, methyl-esterified material was analyzed as described in Cairns et al., *Anal. Biochem.* 199:93–97 (1991).

EXAMPLE 4

Structural Determination of P11.1

The primary structure of P11.1 was determined by automated Edman degradation. Amino acid sequencing revealed the amino acid sequence presented in FIG. 3*a*. The PTH amino acid chromatogram peak for residue 7 (bromotryptophan) eluted just after that of tryptophan. Direct γ-carboxyglutamic acid analysis was also used to help determine the sequence of the peptide. Unlike most conopeptides, the C-terminal carboxyl group of P11.1 is not amidated.

Matrix-assisted laser desorption/ionization mass spectrometry (MALDI-MS) was performed on a Voyager-Elite MALDI-TOF mass spectrometer (Perseptive, Framingham, Mass.) equipped with delayed ion extraction. Spectra were acquired in positive-Ion linear and reflector mode using 2,5-dihydroxybenzoic acid (DHB), α-cyano-4-hydroxycinnamic acid (HCCA) and 2,4,6-trihydroxyacetophenone (THAP) mixed with nitrocellulose as matrices. Sample preparation for MALDI-MS was performed by the dried-droplet method for DHB and the thin layer method for HCCA and THAP/nitrocellulose matrices as described in Kussman et al., *J. Mass. Spectrometry* 32:593–601 (1997). Reduced and alkylated P11.1 1(500 pmoles) in 30 $\mu$l of 50 mM ammonium acetate buffer, pH 6.0, was digested with carboxypeptidase Y (10–20% enzyme, 37° C.). Aliquots were removed after 6, 18, 24, and 48 hours and analyzed directly by MALDI-MS.

Mass spectroscopy demonstrated a molecular mass that was consistent with the amino acid sequence shown in FIG. 3*a,* plus N-acetylgalactosamine-galactose (GalNAc-Gal). Carbohydrate analysis indicated the presence of 0.7 moles each of N-acetyl-galactosamine and galactose per mole of peptide. The mass spectra also showed prompt fragmentation of the peptide indicating the presence of a glycan. The unit is O-linked to the threonine at position 10, as determined by the time course of carboxypeptidase Y digestion monitored by MALDI mass spectrometry. In addition, mass spectrometry revealed that the disaccharide is linked to the peptide by means of the N-acetylgalactosamine moiety.

The mass spectroscopy further revealed that the peptide had the isotope pattern characteristic of bromine. The molecular mass of the reduced and alkylated peptide also showed a mass increase of 232.2 Da compared to that of the native compound, consistent with alkylation of four cysteine residues that are disulfide bonded.

Sufficient amounts of peptide were isolated from the venom of *C. textile* to perform 2D NMR on the natural product. NMR spectra were recorded at 298.3 K and 285.3 K employing a Bruker AMX-500 spectrometer. Homonuclear DFQ-COSY and TOCSY experiments with mixing times of 35 and 50 ms facilitated the spin system assignment. NOESY spectra facilitated identification of intermolecular NOEs and the measurement of $^3J_{HN\alpha}$ coupling constants. Structures were calculated using DGII (InsightII) employing a combination of distance geometry and simulated annealing methodology. Structure determination employed a set of 159 NOE distance restraints (103 intraresidue, 36 sequential, 15 medium and 5 long), 43 $J_{HN\alpha}$ coupling constants and 4 $X_1$ torsion angles. Of 40 structures generated, 38 converged, possessing no distance violation greater than 0.0015 Å and no NOE violation greater than 0.23 Å.

The backbone of P11.1 is highly constrained by the novel intramolecular disulfide bonding arrangement depicted in FIG. 4. The disulfide bond between the cysteine at position 2 and the cysteine at position 8 exists in two slowly converting isomeric forms, increasing the mobility of these two residues without perturbing the overall conformation of the peptide. The presence of bromine at position 6 of the tryptophan ring was confirmed by the TOCSY spectra, as was the hydroxyl group at position 4 of the C-terminal proline. The N-acetylgalactosamine-galactose disaccharide linked to threonine 10 is very mobile, as demonstrated by the increased line width of this residue in the NOESY spectra. The pairwise RMSD over the well-defined backbone residue is 0.43±0.06 Å.

This peptide, with 2 γ-carboxyglutamic acid residues, 1 hydroxyproline residue, 4 cysteine residues, 1 bromotryptophan residue, and a glycosylated threonine residue, has a very high degree of post-translational modification. It contains a well-structured region that begins at residue 1 and extends through the first 9 residues. This region is comprised of two type I β turns and a type II β turn; together, these turns comprise a $3_{10}$ helix. The peptide has an electronegative patch created by the side chains of the two γ-carboxyglutamic acid residues which extend outward from a cleft. This cleft is lined by a hydrophobic region localized around the brominated tryptophan residue, which is enclosed by the glycosylated threonine and the hydroxylated proline.

EXAMPLE 5
Neurotoxic Activity of P11.1

Young mice were subjected to intracerebral injections of increasing amounts of the conopeptide P11.1; behavior patterns were then determined. Following an initial period of somnolence, animals were characterized with intention tremors and local seizure activity. The neurologic effect of P11.1 dissipated over 30 to 60 minutes. The conopeptide did not cause death in any of the animals tested, even at high doses. It is believed that P11.1 dampens the action potential by about 50%, and that it works at the presynaptic membrane.

EXAMPLE 6
Activity of P11.1 at a Cholinergic Synapse of a Buccal Ganglion

The biological activity of the peptide was studied at an identified cholinergic synapse of the buccal ganglion of *Aplysia californica*. Cells were impaled with two low resistance (0.5–2 Megohms) microelectrodes filled with 3 M KCl. The generation of a presynaptic action potential gave rise, in the voltage-clamped postsynaptic neuron at −80 mV, to an inhibitory postsynaptic current (IPSC). Postsynaptic responses were expressed as conductance (nS) by dividing their amplitude (nA) by the driving force (mV). A 3s square depolarization of the voltage-clamped presynaptic neuron induced a postsynaptic response, referred to as long duration-induced postsynaptic current (LDIPSC). The amplitude of evoked miniature postsynaptic currents and the number of quanta (Q) released by the presynaptic neuron were calculated from a statistical analysis of the fluctuations on the top of the LDIPSC. Presynaptic $Ca^{2+}$ currents were elicited by short depolarizing steps (20 ms) from a holding potential of −50 mV to a variety of test potentials. Tetrodotoxin (100 μM) was bath applied to block the inward $Na^+$ current, and outward $K^+$ currents were blocked with extracellular application of tetraethylammonium (50 mM) and 4-aminopyridine (3 mM). The $Ca^{2+}$ gradient was enhanced by raising the extracellular $Ca^{2+}$ concentration to 55 mM. I/V curves were leakage subtracted.

Figure 5A:
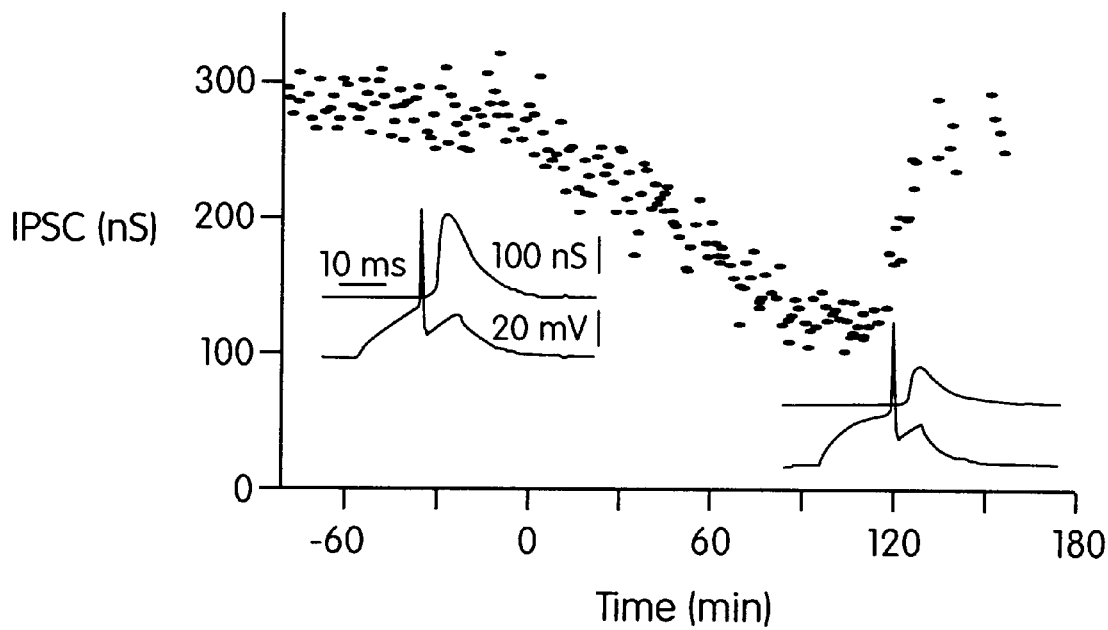
FIG. 5a is a graph showing postsynaptic responses before and after application of P11.1.

In the presence of P11.1 (30 μM), the amplitude of the postsynaptic response (IPSC) evoked by a presynaptic action potential decreased progressively to 40% of the initial value over about 100 min (FIG. 5a). This effect was reversed by washing the preparation with artificial sea water. Inserts in FIG. 5a represent the postsynaptic responses (IPSCs, upper traces) evoked by a presynaptic action potential (lower traces) before (left recordings) and 100 minutes after (right recordings) P11.1 application.

Figure 5B:
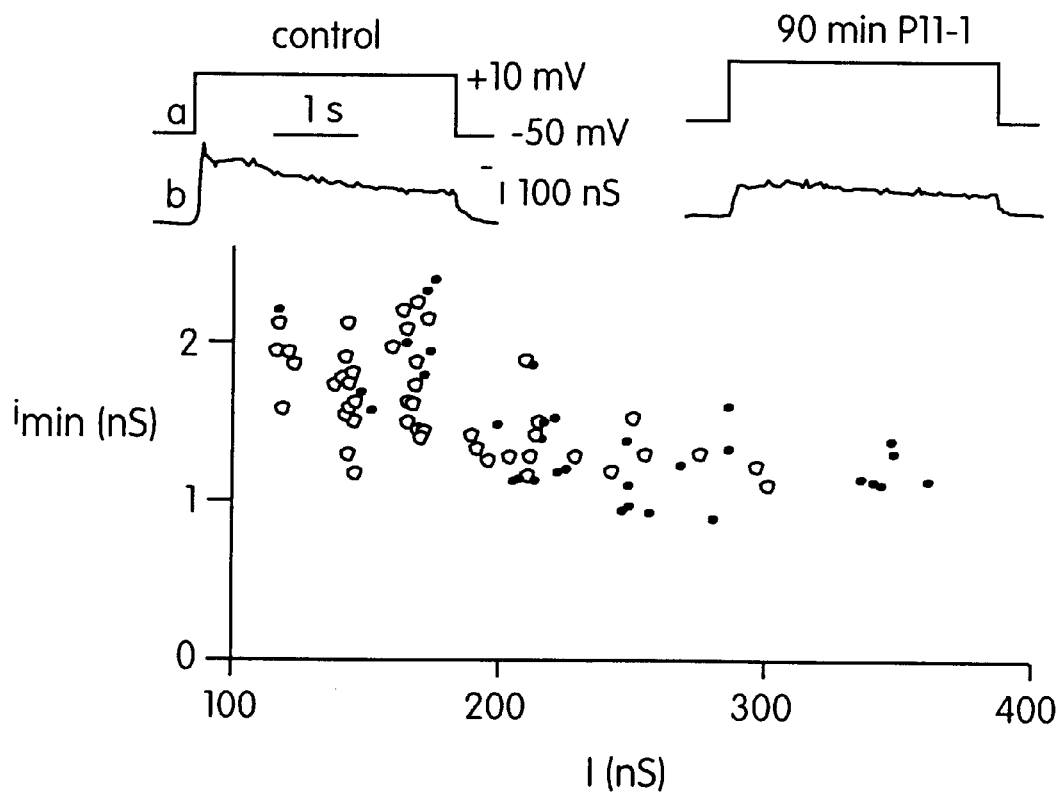
FIG. 5b is a graph showing the amplitude of miniature postsynaptic currents before and after P11.1 application.

FIG. 5b shows the relationship between the mean amplitude of miniature postsynaptic currents ($^i$min, calculated from the above LDIPSCs) and the mean amplitude (I) of the LDIPSC before and 90 minutes after P11.1 application (30 μm). The graph illustrates the decrease in the mean amplitude of the LDIPSC caused by P11.1, due to a reduction in the number of released quanta (60% reduction after 90 minutes). The specificity of this presynaptic effect was further shown by the consistency observed in the mean amplitude of miniature postsynaptic currents. The distribution of mean amplitudes of miniature postsynaptic currents, with respect to the mean amplitude of the LDIPSC, was identical to control values after application of P11.1. This result demonstrated that P11.1 had no effect on postsynaptic acetylcholine (ACh) receptors.

Figure 5C:
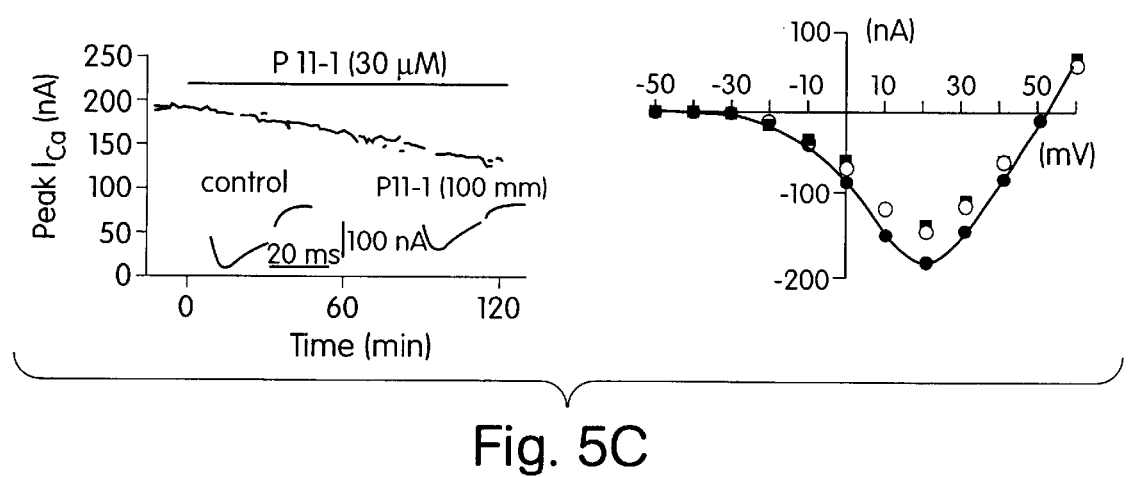
FIG. 5c is a set of graphs showing presynaptic $Ca^{2+}$ current before and after P11.1 application.

In addition, the presynaptic $Ca^{2+}$ current was also decreased after application of P11.1 (to 70% of the control value 120 minutes after application), as shown in FIG. 5c. Because of the relationship between the presynaptic $Ca^{2+}$ influx and the evoked ACh release, the observed reduction in the presynaptic $Ca^{2+}$ current in the presence of P11.1 accounts for the decrease in ACh release.

The left graph shows evolution of the peak presynaptic $Ca^{2+}$ current after bath application of P11.1 (30 μm); the inserts are examples of the $Ca^{2+}$ current before (left) and after (right) P11.1 application. The right graph shows I/V curves representing the presynaptic $Ca^{2+}$ current in the control situation, 90 minutes after, and 115 minutes after, P11.1 application.

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

SEQUENCE LISTING

<160> NUMBER OF SEQ ID NOS: 26

<210> SEQ ID NO: 1
<211> LENGTH: 27
<212> TYPE: PRT
<213> ORGANISM: Conus textile
<220> FEATURE:
<221> NAME/KEY: VARIANT
<222> LOCATION: (1)...(27)
<223> OTHER INFORMATION: Each Xaa is independently selected from Glu and

```
        gamma-carboxyglutamic acid, provided that at least
        one Xaa is gamma-carboxyglutamic acid.
<221> NAME/KEY: VARIANT
<222> LOCATION: (1)...(27)
<223> OTHER INFORMATION: Xaa = Any Amino Acid

<400> SEQUENCE: 1

Asp Val Pro Xaa Ile Val Leu Xaa Phe Met Cys Pro Val Ile Cys Gly
 1               5                  10                  15

Asn Gly Phe Gly Xaa Glu Tyr Cys Asn Cys Thr
             20                  25

<210> SEQ ID NO: 2
<211> LENGTH: 47
<212> TYPE: PRT
<213> ORGANISM: Conus textile
<220> FEATURE:
<221> NAME/KEY: VARIANT
<222> LOCATION: (5)...(16)
<223> OTHER INFORMATION: Each Xaa is independently selected from Glu and
        gamma-carboxyglutamic acid, provided that at least
        one Xaa is gamma-carboxyglutamic acid.
<221> NAME/KEY: VARIANT
<222> LOCATION: (1)...(47)
<223> OTHER INFORMATION: Xaa = Any Amino Acid
<221> NAME/KEY: VARIANT
<222> LOCATION: (1)...(47)
<223> OTHER INFORMATION: Xaa = Any Amino Acid

<400> SEQUENCE: 2

Ser Cys Asp Ser Xaa Phe Ser Ser Xaa Phe Cys Xaa Arg Pro Xaa Xaa
 1               5                  10                  15

Ser Cys Ser Cys Ser Thr His Thr Cys Cys His Trp Ala Arg Arg Asp
             20                  25                  30

Gln Cys Met Lys Pro Gln Arg Cys Ile Ser Ala Gln Lys Gly Asn
         35                  40                  45

<210> SEQ ID NO: 3
<211> LENGTH: 19
<212> TYPE: PRT
<213> ORGANISM: Conus textile
<220> FEATURE:
<221> NAME/KEY: VARIANT
<222> LOCATION: (2)...(16)
<223> OTHER INFORMATION: Pro at position 2 is 4Hyp and each Xaa is
        independently selected from Glu and
        gamma-carboxyglutamic acid, provided that at least
        one Xaa is gamma-carboxyglutamic acid.
<221> NAME/KEY: VARIANT
<222> LOCATION: (1)...(19)
<223> OTHER INFORMATION: Xaa = Any Amino Acid
<221> NAME/KEY: VARIANT
<222> LOCATION: (1)...(19)
<223> OTHER INFORMATION: Xaa = Any Amino Acid

<400> SEQUENCE: 3

Arg Pro Xaa Cys Cys Ser Asp Pro Arg Cys Asn Ser Ser His Pro Xaa
 1               5                  10                  15

Leu Cys Gly

<210> SEQ ID NO: 4
<211> LENGTH: 27
<212> TYPE: PRT
<213> ORGANISM: Conus textile
<220> FEATURE:
<221> NAME/KEY: VARIANT
<222> LOCATION: (8)...(13)
<223> OTHER INFORMATION: Each Xaa is independently selected from Glu and
        gamma-carboxyglutamic acid, provided that at least
```

```
       one Xaa is gamma-carboxyglutamic acid.
<221> NAME/KEY: VARIANT
<222> LOCATION: (1)...(27)
<223> OTHER INFORMATION: Xaa = Any Amino Acid
<221> NAME/KEY: VARIANT
<222> LOCATION: (1)...(27)
<223> OTHER INFORMATION: Xaa = Any Amino Acid

<400> SEQUENCE: 4

Gly Cys Asn Asn Ser Cys Gln Xaa His Ser Asp Cys Xaa Ser His Cys
 1               5                  10                  15

Ile Cys Thr Phe Arg Gly Cys Gly Ala Val Asn
            20                  25

<210> SEQ ID NO: 5
<211> LENGTH: 29
<212> TYPE: PRT
<213> ORGANISM: Conus textile
<220> FEATURE:
<221> NAME/KEY: VARIANT
<222> LOCATION: (4)...(4)
<223> OTHER INFORMATION: Xaa is gamma-carboxyglutamic acid

<400> SEQUENCE: 5

Cys Ile Pro Xaa Gly Ser Ser Cys Ser Ser Gly Ser Cys Cys His
 1               5                  10                  15

Lys Ser Cys Cys Arg Trp Thr Cys Asn Gln Pro Cys Leu
            20                  25

<210> SEQ ID NO: 6
<211> LENGTH: 31
<212> TYPE: PRT
<213> ORGANISM: Conus textile
<220> FEATURE:
<221> NAME/KEY: VARIANT
<222> LOCATION: (3)...(31)
<223> OTHER INFORMATION: Xaa in positions 3 and 31 is independently
      selected from Trp and bromotryptophan; Xaa in
      positions 5, 18, 22, and 25 is independently
      selected from Glu and gamma-carboxyglutamic acid,

<400> SEQUENCE: 6

Gly Met Xaa Gly Xaa Cys Lys Asp Gly Leu Thr Thr Cys Leu Ala Pro
 1               5                  10                  15

Ser Xaa Cys Cys Ser Xaa Asp Cys Xaa Gly Ser Cys Thr Met Xaa
            20                  25                  30

<210> SEQ ID NO: 7
<211> LENGTH: 13
<212> TYPE: PRT
<213> ORGANISM: Conus textile
<220> FEATURE:
<221> NAME/KEY: VARIANT
<222> LOCATION: (1)...(13)
<223> OTHER INFORMATION: Xaa in positions 1 and 4 is independently
      selected from Glu and gamma-carboxyglutamic acid, provided
      that at least one of Xaa in positions 1 and 4 is
      gamma-carboxyglutamic acid; Xaa in position 7 is

<400> SEQUENCE: 7

Xaa Cys Cys Xaa Asp Gly Xaa Cys Cys Thr Ala Ala Pro
 1               5                  10

<210> SEQ ID NO: 8
<211> LENGTH: 25
<212> TYPE: PRT
<213> ORGANISM: Conus textile
<220> FEATURE:
```

```
<221> NAME/KEY: VARIANT
<222> LOCATION: (10)...(18)
<223> OTHER INFORMATION: Xaa at position 10 is gamma-carboxyglutamic
      acid; Pro at position 12 is Pro or 4Hyp; Xaa at position
      18 is Trp or bromotryptophan.

<400> SEQUENCE: 8

Ser Cys Ser Asp Asp Trp Gln Tyr Cys Xaa Ser Pro Thr Asp Cys Cys
1               5                   10                  15

Ser Xaa Asp Cys Asp Val Val Cys Ser
            20                  25

<210> SEQ ID NO: 9
<211> LENGTH: 10
<212> TYPE: PRT
<213> ORGANISM: Conus textile
<220> FEATURE:
<221> NAME/KEY: VARIANT
<222> LOCATION: (2)...(9)
<223> OTHER INFORMATION: Xaa at position 2 is Trp or bromotryptophan;
      Pro at positions 5 and 7 is independently selected
      from Pro and 4Hyp; Xaa at position 9 is
      gamma-carboxyglutamic acid.

<400> SEQUENCE: 9

Ala Xaa Cys His Pro Cys Pro Phe Xaa Tyr
1               5                   10

<210> SEQ ID NO: 10
<211> LENGTH: 25
<212> TYPE: PRT
<213> ORGANISM: Conus textile
<220> FEATURE:
<221> NAME/KEY: VARIANT
<222> LOCATION: (1)...(25)
<223> OTHER INFORMATION: Pro at position 12 is Pro or 4Hyp; Xaa at
      position 18 is Trp or bromotryptophan; Xaa at position 10
      is Pro or hydroxyproline.

<400> SEQUENCE: 10

Asn Cys Ser Asp Asp Trp Gln Tyr Cys Xaa Ser Pro Ser Asp Cys Cys
1               5                   10                  15

Ser Xaa Asp Cys Asp Val Val Cys Ser
            20                  25

<210> SEQ ID NO: 11
<211> LENGTH: 27
<212> TYPE: PRT
<213> ORGANISM: Conus textile
<220> FEATURE:
<221> NAME/KEY: VARIANT
<222> LOCATION: (3)...(18)
<223> OTHER INFORMATION: Pro at positions 3 and 8 is independently
      selected from Pro and 4Hyp; Xaa at positions 7 and 14 is
      independently selected from Glu and
      gamma-carboxyglutamic acid, provided that at least
<221> NAME/KEY: VARIANT
<222> LOCATION: (1)...(27)
<223> OTHER INFORMATION: Xaa = Any Amino Acid
<221> NAME/KEY: VARIANT
<222> LOCATION: (1)...(27)
<223> OTHER INFORMATION: Xaa = Any Amino Acid

<400> SEQUENCE: 11

Leu Cys Pro Asp Tyr Thr Xaa Pro Cys Ser His Ala His Xaa Cys Cys
1               5                   10                  15

Ser Xaa Asn Cys Tyr Asn Gly His Cys Thr Gly
            20                  25
```

<210> SEQ ID NO: 12
<211> LENGTH: 27
<212> TYPE: PRT
<213> ORGANISM: Conus textile
<220> FEATURE:
<221> NAME/KEY: VARIANT
<222> LOCATION: (4)...(21)
<223> OTHER INFORMATION: Each Xaa is gamma-carboxyglutamic acid.
<221> NAME/KEY: VARIANT
<222> LOCATION: (1)...(27)
<223> OTHER INFORMATION: Xaa = Any Amino Acid
<221> NAME/KEY: VARIANT
<222> LOCATION: (1)...(27)
<223> OTHER INFORMATION: Xaa = Any Amino Acid

<400> SEQUENCE: 12

Asp Val Pro Xaa Ile Val Leu Xaa Phe Met Cys Pro Val Ile Cys Gly
 1               5                  10                  15

Asn Gly Phe Gly Xaa Glu Tyr Cys Asn Cys Thr
             20                  25

<210> SEQ ID NO: 13
<211> LENGTH: 47
<212> TYPE: PRT
<213> ORGANISM: Conus textile
<220> FEATURE:
<221> NAME/KEY: VARIANT
<222> LOCATION: (5)...(16)
<223> OTHER INFORMATION: Each Xaa is gamma-carboxyglutamic acid.
<221> NAME/KEY: VARIANT
<222> LOCATION: (1)...(47)
<223> OTHER INFORMATION: Xaa = Any Amino Acid
<221> NAME/KEY: VARIANT
<222> LOCATION: (1)...(47)
<223> OTHER INFORMATION: Xaa = Any Amino Acid

<400> SEQUENCE: 13

Ser Cys Asp Ser Xaa Phe Ser Ser Xaa Phe Cys Xaa Arg Pro Xaa Xaa
 1               5                  10                  15

Ser Cys Ser Cys Ser Thr His Thr Cys Cys His Trp Ala Arg Arg Asp
             20                  25                  30

Gln Cys Met Lys Pro Gln Arg Cys Ile Ser Ala Gln Lys Gly Asn
         35                  40                  45

<210> SEQ ID NO: 14
<211> LENGTH: 19
<212> TYPE: PRT
<213> ORGANISM: Conus textile
<220> FEATURE:
<221> NAME/KEY: VARIANT
<222> LOCATION: (2)...(16)
<223> OTHER INFORMATION: Pro at position 2 is 4Hyp and Xaa at positions
      3 and 16 is gamma-carboxyglutamic acid.
<221> NAME/KEY: VARIANT
<222> LOCATION: (1)...(19)
<223> OTHER INFORMATION: Xaa = Any Amino Acid
<221> NAME/KEY: VARIANT
<222> LOCATION: (1)...(19)
<223> OTHER INFORMATION: Xaa = Any Amino Acid

<400> SEQUENCE: 14

Arg Pro Xaa Cys Cys Ser Asp Pro Arg Cys Asn Ser Ser His Pro Xaa
 1               5                  10                  15

Leu Cys Gly

<210> SEQ ID NO: 15
<211> LENGTH: 27
<212> TYPE: PRT

```
<213> ORGANISM: Conus textile
<220> FEATURE:
<221> NAME/KEY: VARIANT
<222> LOCATION: (8)...(13)
<223> OTHER INFORMATION: Each Xaa is gamma-carboxyglutamic acid.
<221> NAME/KEY: VARIANT
<222> LOCATION: (1)...(27)
<223> OTHER INFORMATION: Xaa = Any Amino Acid
<221> NAME/KEY: VARIANT
<222> LOCATION: (1)...(27)
<223> OTHER INFORMATION: Xaa = Any Amino Acid

<400> SEQUENCE: 15

Gly Cys Asn Asn Ser Cys Gln Xaa His Ser Asp Cys Xaa Ser His Cys
 1               5                  10                  15

Ile Cys Thr Phe Arg Gly Cys Gly Ala Val Asn
            20                  25

<210> SEQ ID NO: 16
<211> LENGTH: 29
<212> TYPE: PRT
<213> ORGANISM: Conus textile
<220> FEATURE:
<221> NAME/KEY: VARIANT
<222> LOCATION: (4)...(4)
<223> OTHER INFORMATION: Xaa is gamma-carboxyglutamic acid.

<400> SEQUENCE: 16

Cys Ile Pro Xaa Gly Ser Ser Cys Ser Ser Ser Gly Ser Cys Cys His
 1               5                  10                  15

Lys Ser Cys Cys Arg Trp Thr Cys Asn Gln Pro Cys Leu
            20                  25

<210> SEQ ID NO: 17
<211> LENGTH: 31
<212> TYPE: PRT
<213> ORGANISM: Conus textile
<220> FEATURE:
<221> NAME/KEY: VARIANT
<222> LOCATION: (3)...(31)
<223> OTHER INFORMATION: Xaa at positions 3 and 31 is bromotyptophan;
      Xaa at positions 5, 18, 22, and 25 is
      gamma-carboxyglutamic acid; Pro at position 16 is
      4Hyp.

<400> SEQUENCE: 17

Gly Met Xaa Gly Xaa Cys Lys Asp Gly Leu Thr Thr Cys Leu Ala Pro
 1               5                  10                  15

Ser Xaa Cys Cys Ser Xaa Asp Cys Xaa Gly Ser Cys Thr Met Xaa
            20                  25                  30

<210> SEQ ID NO: 18
<211> LENGTH: 13
<212> TYPE: PRT
<213> ORGANISM: Conus textile
<220> FEATURE:
<221> NAME/KEY: VARIANT
<222> LOCATION: (1)...(13)
<223> OTHER INFORMATION: Xaa at positions 1 and 4 is
      gamma-carboxyglutamic acid; Xaa at position 7 is bromotryptophan;
      Pro at position 13 is 4Hyp.

<400> SEQUENCE: 18

Xaa Cys Cys Xaa Asp Gly Xaa Cys Cys Thr Ala Ala Pro
 1               5                  10

<210> SEQ ID NO: 19
<211> LENGTH: 25
```

```
<212> TYPE: PRT
<213> ORGANISM: Conus textile
<220> FEATURE:
<221> NAME/KEY: VARIANT
<222> LOCATION: (10)...(18)
<223> OTHER INFORMATION: Xaa at position 10 is gamma-carboxyglutamic
      acid; Pro at position 12 is 4Hyp; Xaa at position 18 is
      bromotryptophan.

<400> SEQUENCE: 19

Ser Cys Ser Asp Asp Trp Gln Tyr Cys Xaa Ser Pro Thr Asp Cys Cys
 1               5                  10                  15

Ser Xaa Asp Cys Asp Val Val Cys Ser
            20                  25

<210> SEQ ID NO: 20
<211> LENGTH: 10
<212> TYPE: PRT
<213> ORGANISM: Conus textile
<220> FEATURE:
<221> NAME/KEY: VARIANT
<222> LOCATION: (2)...(9)
<223> OTHER INFORMATION: Xaa at position 2 is bromotryptophan; Pro at
      positions 5 and 7 is 4Hyp; Xaa at position 9 is
      gamma-carboxyglutamic acid.

<400> SEQUENCE: 20

Ala Xaa Cys His Pro Cys Pro Phe Xaa Tyr
 1               5                  10

<210> SEQ ID NO: 21
<211> LENGTH: 25
<212> TYPE: PRT
<213> ORGANISM: Conus textile
<220> FEATURE:
<221> NAME/KEY: VARIANT
<222> LOCATION: (10)...(18)
<223> OTHER INFORMATION: Xaa at position 10 is gamma-carboxyglutamic
      acid; Pro at position 12 is 4Hyp; Xaa at position 18 is
      bromotryptophan.

<400> SEQUENCE: 21

Asn Cys Ser Asp Asp Trp Gln Tyr Cys Xaa Ser Pro Ser Asp Cys Cys
 1               5                  10                  15

Ser Xaa Asp Cys Asp Val Val Cys Ser
            20                  25

<210> SEQ ID NO: 22
<211> LENGTH: 27
<212> TYPE: PRT
<213> ORGANISM: Conus textile
<220> FEATURE:
<221> NAME/KEY: VARIANT
<222> LOCATION: (3)...(18)
<223> OTHER INFORMATION: Pro at positions 3 and 8 is 4Hyp; Xaa at
      positions 7 and 14 is gamma-carboxyglutamic acid; Xaa at
      position 18 is bromotryptophan.
<221> NAME/KEY: VARIANT
<222> LOCATION: (1)...(27)
<223> OTHER INFORMATION: Xaa = Any Amino Acid
<221> NAME/KEY: VARIANT
<222> LOCATION: (1)...(27)
<223> OTHER INFORMATION: Xaa = Any Amino Acid

<400> SEQUENCE: 22

Leu Cys Pro Asp Tyr Thr Xaa Pro Cys Ser His Ala His Xaa Cys Cys
 1               5                  10                  15

Ser Xaa Asn Cys Tyr Asn Gly His Cys Thr Gly
            20                  25
```

```
<210> SEQ ID NO: 23
<211> LENGTH: 17
<212> TYPE: PRT
<213> ORGANISM: Conus geographus
<220> FEATURE:
<221> NAME/KEY: VARIANT
<222> LOCATION: (1)...(17)
<223> OTHER INFORMATION: Xaa is gamma-carboyglutamic acid

<400> SEQUENCE: 23

Gly Glu Xaa Xaa Leu Gln Xaa Asn Gln Xaa Leu Ile Arg Xaa Lys Ser
 1               5                  10                  15

Asn

<210> SEQ ID NO: 24
<211> LENGTH: 21
<212> TYPE: PRT
<213> ORGANISM: Conus tulipa
<220> FEATURE:
<221> NAME/KEY: VARIANT
<222> LOCATION: (1)...(21)
<223> OTHER INFORMATION: Xaa is gamma-carboxyglutamic acid

<400> SEQUENCE: 24

Gly Glu Xaa Xaa Tyr Gln Lys Met Leu Xaa Asn Leu Arg Xaa Ala Glu
 1               5                  10                  15

Val Lys Lys Asn Ala
            20

<210> SEQ ID NO: 25
<211> LENGTH: 27
<212> TYPE: PRT
<213> ORGANISM: Conus textile
<220> FEATURE:
<221> NAME/KEY: VARIANT
<222> LOCATION: (1)...(27)
<223> OTHER INFORMATION: Xaa is gamma-carboxyglutamic acid

<400> SEQUENCE: 25

Cys Gly Gly Tyr Ser Thr Tyr Cys Xaa Val Asp Ser Xaa Cys Cys Ser
 1               5                  10                  15

Asp Asn Cys Val Arg Ser Tyr Cys Thr Leu Phe
            20                  25

<210> SEQ ID NO: 26
<211> LENGTH: 13
<212> TYPE: PRT
<213> ORGANISM: Conus textile
<220> FEATURE:
<221> NAME/KEY: VARIANT
<222> LOCATION: (1)...(4)
<223> OTHER INFORMATION: Xaa is gamma-carboxyglutamic acid
<221> NAME/KEY: VARIANT
<222> LOCATION: (7)...(7)
<223> OTHER INFORMATION: Xaa is bromotryptophan
<221> NAME/KEY: VARIANT
<222> LOCATION: (10)...(10)
<223> OTHER INFORMATION: Thr is post-translationally modified with a
      N-acetylgalactosamine-galactose disaccharide
<221> NAME/KEY: VARIANT
<222> LOCATION: (13)...(13)
<223> OTHER INFORMATION: Pro is 4Hyp

<400> SEQUENCE: 26

Xaa Cys Cys Xaa Asp Gly Xaa Cys Cys Thr Ala Ala Pro
 1               5                  10
```

What is claimed is:

1. A substantially pure peptide having the amino acid sequence:

Asp Val Pro $X_1$ Ile Val Leu $X_2$ Phe Met Cys Pro Val Ile Cys Gly Asn Gly Phe Gly $X_3$ Glu Tyr Cys Asn Cys Thr (SEQ ID NO:1), wherein each of $X_1$, $X_2$, and $X_3$ is independently selected from Glu and Gla, provided that at least one of $X_1$, $X_2$, and $X_3$ is Gla.

2. A substantially pure peptide having the amino acid sequence:

Ser Cys Asp Ser $X_4$ Phe Ser Ser $X_5$ Phe Cys $X_6$ Arg Pro $X_7$ $X_8$ Ser Cys Ser Cys Ser Thr His Thr Cys Cys His Trp Ala Arg Arg Asp Gln Cys Met Lys Pro Gln Arg Cys Ile Ser Ala Gln Lys Gly Asn (SEQ ID NO:2), wherein each of $X_4$, $X_5$, $X_6$, $X_7$, and $X_8$ is independently selected from Glu and Gla, provided that at least one of $X_4$, $X_5$, $X_6$, $X_7$, and $X_8$ is Gla.

3. A substantially pure peptide having the amino acid sequence:

Arg $X_9$ $X_{10}$ Cys Cys Ser Asp Pro Arg Cys Asn Ser Ser His Pro $X_{11}$ Leu Cys Gly (SEQ ID NO:3), wherein $X_9$ is Pro or OHP and each of $X_{10}$ and $X_{11}$ is independently selected from Glu and Gla, provided that at least one of $X_{10}$ and $X_{11}$ is Gla.

4. The peptide of claim 3, wherein the C-terminus is amidated.

5. A substantially pure peptide having the amino acid sequence:

Gly Cys Asn Asn Ser Cys Gln $X_{12}$ His Ser Asp Cys $X_{13}$ Ser His Cys Ile Cys Thr Phe Arg Gly Cys Gly Ala Val Asn (SEQ ID NO:4), wherein each of $X_{12}$ and $X_{13}$ is independently selected from Glu and Gla, provided that at least one of $X_{12}$ and $X_{13}$ is Gla.

6. The peptide of claim 5, wherein the C terminus is amidated.

7. A substantially pure peptide having the amino acid sequence:

Cys Ile Pro Gla Gly Ser Ser Cys Ser Ser Ser Gly Ser Cys Cys His Lys Ser Cys Cys Arg Trp Thr Cys Asn Gln Pro Cys Leu (SEQ ID NO:5).

8. A substantially pure peptide having the amino acid sequence:

Gly Met $X_{14}$ Gly $X_{15}$ Cys Lys Asp Gly Leu Thr Thr Cys Leu Ala $X_{16}$ Ser $X_{17}$ Cys Cys Ser $X_{18}$ Asp Cys $X_{19}$ Gly Ser Cys Thr Met $X_{20}$ (SEQ ID NO:6), wherein each of $X_{14}$ and $X_{20}$ is independently selected from Trp and BrW, each Of $X_{15}$, $X_{17}$, $X_{18}$, and $X_{19}$ is independently selected from Glu and Gla, provided that at least one of $X_{15}$, $X_{17}$, $X_{18}$, and $X_{19}$ is Gla, and $X_{16}$ is Pro or OHP.

9. A substantially pure peptide having the amino acid sequence:

$X_{21}$ Cys Cys $X_{22}$ Asp Gly $X_{23}$ Cys Cys Thr Ala Ala $X_{24}$ (SEQ ID NO:7), wherein each of $X_{21}$ and $X_{22}$ is independently selected from Glu and Gla, provided that at least one of $X_{21}$ and $X_{22}$ is Gla, $X_{23}$ is Trp or BrW, and $X_{24}$ is Pro or OHP.

10. The peptide of claim 9, wherein the Thr is glycosylated.

11. A substantially pure peptide having the amino acid sequence:

Ser Cys Ser Asp Asp Trp Gln Tyr Cys Gla Ser $X_{25}$ Thr Asp Cys Cys Ser $X_{26}$ Asp Cys Asp Val Val Cys Ser (SEQ ID NO:8), wherein $X_{25}$ is Pro or OHP and $X_{26}$ is Trp or BrW.

12. A substantially pure peptide having the amino acid sequence:

Ala $X_{27}$ Cys His $X_{28}$ Cys $X_{29}$ Phe Gla Tyr (SEQ ID NO:9), wherein $X_{27}$ is Trp or BrW and each of $X_{28}$ and $X_{29}$ is independently selected from Pro and OHP.

13. A substantially pure peptide having the amino acid sequence:

Asn Cys Ser Asp Asp Trp Gln Tyr Cys Gla Ser $X_{30}$ Ser Asp Cys Cys Ser $X_{31}$ Asp Cys Asp Val Val Cys Ser (SEQ ID NO:10), wherein $X_{30}$ is Pro or OHP and $X_{31}$ is Trp or BrW.

14. A substantially pure peptide having the amino acid sequence:

Leu Cys $X_{32}$ Asp Tyr Thr $X_{33}$ $X_{34}$ Cys Ser His Ala His $X_{35}$ Cys Cys Ser $X_{36}$ Asn Cys Tyr Asn Gly His Cys Thr Gly (SEQ ID NO:11), wherein each of $X_{32}$ and $X_{34}$ is independently selected from Pro and OHP, and each of $X_{33}$ and $X_{35}$ is independently selected from Glu and Gla, provided that at least one of $X_{33}$ and $X_{35}$ is Gla, and $X_{36}$ is Trp or BrW.

* * * * *

UNITED STATES PATENT AND TRADEMARK OFFICE
CERTIFICATE OF CORRECTION

PATENT NO. : 6,307,014 B1
DATED : October 23, 2001
INVENTOR(S) : Bruce Furie, Barbara Furie, John Stenflo, Alan C. Rigby and Peter Roepstorff It is certified that error appears in the above-identified patent and that said Letters Patent is hereby corrected as shown below:

Title page,
Item [73] TheAssignee should read -- Marine Biological Laboratory, Woods Hole, Massachusetts --

Column 1,
Line 62, delete "$X_3$" and insert -- $X_{13}$ --.

Column 6,
Line 11, delete "1(500" and insert -- (500 --.

Column 24,
Line 3, delete "Of" and insert -- of --.

Signed and Sealed this

Sixteenth Day of July, 2002

Attest:

JAMES E. ROGAN
Attesting Officer  Director of the United States Patent and Trademark Office